US011887736B1

(12) United States Patent
Norgeot et al.

(10) Patent No.: US 11,887,736 B1
(45) Date of Patent: Jan. 30, 2024

(54) METHODS FOR EVALUATING CLINICAL COMPARATIVE EFFICACY USING REAL-WORLD HEALTH DATA AND ARTIFICIAL INTELLIGENCE

(71) Applicant: Anthem , Inc., Indianapolis, IN (US)

(72) Inventors: Beau Norgeot, Los Gatos, CA (US); Theodore Goldstein, Los Altos, CA (US); Axel Bernal, Sunnyvale, CA (US); Chinmay Belthangady, San Jose, CA (US); Herman Sahota, Mountain View, CA (US); Nicholas Guggemos, Belmont, CA (US); Paula Alves, San Francisco, CA (US); Rajas Kale, San Francisco, CA (US); Stefanos Giampanis, Redwood City, CA (US); William Stedden, Daly City, CA (US); Rachel Lissak, Mountain View, CA (US); Bobby Samuel, Santa Clara, CA (US)

(73) Assignee: ELEVANCE HEALTH, INC., Indianapolis, IN (US)

( * ) Notice: Subject to any disclaimer, the term of this patent is extended or adjusted under 35 U.S.C. 154(b) by 320 days.

(21) Appl. No.: 17/147,415

(22) Filed: Jan. 12, 2021

Related U.S. Application Data

(60) Provisional application No. 63/003,524, filed on Apr. 1, 2020.

(51) Int. Cl.
G16H 50/30 (2018.01)
G16H 15/00 (2018.01)
(Continued)

(52) U.S. Cl.
CPC ............. *G16H 50/30* (2018.01); *G16H 10/60* (2018.01); *G16H 15/00* (2018.01); *G16H 50/70* (2018.01)

(58) Field of Classification Search
CPC ........ G16H 50/30; G16H 10/60; G16H 15/00; G16H 50/70; G16H 50/00; G16H 10/00; G06Q 50/20–26
See application file for complete search history.

(56) References Cited

U.S. PATENT DOCUMENTS

| 10,946,311 | B1 * | 3/2021 | McNair | ............. B01D 15/3809 |
| 2010/0177950 | A1 * | 7/2010 | Donovan | ............... G16H 50/30 702/19 |

(Continued)

*Primary Examiner* — Neal Sereboff
(74) *Attorney, Agent, or Firm* — Morgan, Lewis & Bockius LLP

(57) ABSTRACT

Systems and methods for evaluating clinical comparative efficacy using real-world health data are provided herein. The method includes obtaining health trajectories for members of a healthcare system. The method also includes identifying index events in the health trajectories, and segmenting the health trajectories with index events into sub-trajectories such that each sub-trajectory ends at a different index event. The method also includes generating a digital fingerprint for each sub-trajectory by either (i) generating a raw data vector, or (ii) applying representation learning to generate an embedding vector. The method also includes identifying sub-trajectories that are similar to a patient sub-trajectory by either (i) performing a stratified search, or (ii) performing a nearest-neighbor search on the embedding vectors of the members. The method also includes ranking treatment strategies for the patient based on outcomes of the treatment strategies, according to the identified similar sub-trajectories.

16 Claims, 6 Drawing Sheets

(51) Int. Cl.
*G16H 50/70* (2018.01)
*G16H 10/60* (2018.01)

(56) References Cited

U.S. PATENT DOCUMENTS

| | | | |
|---|---|---|---|
| 2013/0080134 A1* | 3/2013 | Donovan | G16H 50/50 |
| | | | 703/11 |
| 2014/0025398 A1* | 1/2014 | Ridgeway | G16H 50/20 |
| | | | 705/3 |
| 2018/0247713 A1* | 8/2018 | Rothman | A61B 5/02055 |
| 2019/0066843 A1* | 2/2019 | Carlson | G16H 10/60 |
| 2020/0105413 A1* | 4/2020 | Vladimirova | G16H 50/30 |
| 2021/0090694 A1* | 3/2021 | Colley | G16H 50/70 |
| 2021/0210189 A1* | 7/2021 | Casey | A61B 34/10 |
| 2021/0249132 A1* | 8/2021 | Colborn | G16H 50/30 |
| 2021/0391079 A1* | 12/2021 | Clifton | A61B 5/7275 |

\* cited by examiner

US 11,887,736 B1

METHODS FOR EVALUATING CLINICAL COMPARATIVE EFFICACY USING REAL-WORLD HEALTH DATA AND ARTIFICIAL INTELLIGENCE

CROSS-REFERENCE TO RELATED APPLICATIONS

This application claims the benefit of U.S. Provisional Patent Application No. 63/003,524 filed on Apr. 1, 2010 entitled "Methods for Evaluating Clinical Comparative Efficacy Using Real-World Health Data and Artificial Intelligence", which is incorporated by reference herein in its entirety.

TECHNICAL FIELD

The disclosed implementations relate generally to healthcare applications and more specifically to a method, system, and device for evaluating clinical comparative efficacy for healthcare.

BACKGROUND

Current clinical practice follows a trial-and-error approach that can be frustrating for patients. When a patient is prescribed a treatment, one of three situations may occur. First, it is possible that the treatment leads to poorer lab results, thereby leading to removal of that medication from the regimen and trialing a new one, while all previous treatment regimens continue. As a second possibility, if the treatment does not change lab results, an additional medication is trialed. A third outcome could be that the treatment is successful at improving lab results, and the treatment regimen is continued. Even if this trial-and-error approach results in a successful treatment, it requires a patient to endure treatment failures. For example, the patient may need to wait to visit their provider several times, make multiple lab visits, and test different treatments before a successful regimen is found. Meanwhile, insurance claims accrue, and medical costs rise.

Although novel drugs go through rigorous Randomized Controlled Trials (RCT) for FDA approval before going to market, real-world usages of these drugs are often not studied. Variations in dosages, frequencies, patient co-morbidities, and drug interactions are often not well characterized and can lead to suboptimal to fatal responses. When a provider makes a treatment recommendation, many of these variations are not fully considered. Moreover, conventional practice fails to take into account outcomes of treatment options on other members of a healthcare system.

SUMMARY

Accordingly, there is a need for data driven (or real-world evidence-based) methods, systems, and/or devices that leverage healthcare data for members of a healthcare system to predict effective treatment options. The techniques described herein can help patients receive fewer and more effective treatment interventions. Systems that incorporate such techniques can help improve overall clinical experience and can lead to a better healthcare system as a whole.

In one aspect, some implementations include a computer-implemented method of evaluating clinical comparative efficacy using real-world health data. The method is executed at a computing device coupled to one or more memory units each operable to store at least one program. One or more servers having at least one processor communicatively coupled to the one or more memory units, in which the at least one program, when executed by the at least one processor, causes the at least one processor to perform the method.

The method includes obtaining health trajectories for members of a healthcare system. Each health trajectory corresponds to a respective member and represents time-ordered series of events for the respective member, and each event represents an interaction between the respective member and the healthcare system. The method also includes identifying index events in the health trajectories for the members. An index event is any clinical or health data point. The method also includes segmenting the health trajectories with index events into a plurality of sub-trajectories such that each sub-trajectory ends or terminates at a different index event. The method also includes generating a digital fingerprint for each sub-trajectory by either (i) generating a raw data vector from raw trajectories data representing the health trajectories, or (ii) applying representation learning to generate an embedding vector. The method also includes identifying one or more sub-trajectories that are similar to a patient sub-trajectory by either (i) performing a stratified search to select the one or more sub-trajectories from the plurality of sub-trajectories based on one or more stratifying criteria, or (ii) performing a nearest-neighbor search on the embedding vectors of the members. The patient sub-trajectory corresponds to a patient member of the healthcare system. The method also includes ranking treatment strategies that are most likely to be efficacious for the patient member based on outcomes associated with each of the treatment strategies, according to the one or more sub-trajectories.

In some implementations, generating the digital fingerprints includes mapping raw data encodings of distinct member features for the members that includes demographic, clinical data, and laboratory data.

In some implementations, applying representation learning algorithm includes performing matrix factorization to the raw trajectories data to convert the raw trajectories data to a vector of floating point numbers. Performing the matrix factorization includes: generating a sparse matrix, wherein each row of the sparse matrix represents a respective sub-trajectory, and each column represents a respective claim code representing a respective event; and factorizing the sparse matrix using Alternating Least Squares (ALS) to obtain a first factor that includes trajectory embedding matrix and a second factor that includes code embedding matrix. One axis of the trajectory embedding matrix correspond to floating-point vector representations of the plurality of sub-trajectories, and one axis of the code embedding matrix correspond to floating-point representations of claim codes.

In some implementations, applying representation learning comprises, performing a sequence of steps for each sub-trajectory of the plurality of sub-trajectories. The sequence of steps includes: obtaining code embeddings corresponding to claim codes representing events in the sub-trajectory; inputting the code embeddings to a trained sequence model to obtain hidden states for different layers for a terminal index event for the sub-trajectory; and combining the hidden states for the different layers to obtain the embedding vectors for the sub-trajectory. In some implementations, obtaining the code embeddings include learning the code embeddings using the claim codes via machine-learning functionality. In some implementations, obtaining the code embeddings includes generating the code embeddings using a code embedding model selected from the group consisting of: a matrix-factorization model, a skip-gram model, and a continuous-bag-of-words model. In some implementations, the trained sequence model is trained on the health trajectories with a target selected from the group consisting of: a next code for a predetermined health trajectory; a real number or a set of real numbers which reflects overall health of a predetermined member or a set of members; a real number representing a lab value for a predetermined lab event or a measured value for a predetermined EMR event; and a presence of a predetermined code within a specified time window.

In some implementations, performing the nearest-neighbor search is performed using k-Nearest Neighbors (k-NN) and includes hyper-parameter tuning for number of nearest neighbors and distance to similar neighbors.

In some implementations, the stratifying criteria is selected from the group consisting of: use of same prior drugs as the patient member; use of same prior drugs and having similar prior lab results as the patient member; use of same prior drugs and having similar demography as the patient member; and present same set of co-morbidities relevant to a disease.

In some implementations, the method further includes, prior to identifying the one or more sub-trajectories, tuning hyper-parameters for the nearest-neighbor search or the stratified search by performing a sequence of steps. The sequence of steps includes selecting a seed member from the members of the healthcare system. The sequence of steps also includes identifying a seed sub-trajectory from the plurality of sub-trajectories, wherein the seed sub-trajectory corresponds to the seed member, and the seed sub-trajectory is not the most recent sub-trajectory for the seed member. The sequence of steps also includes performing either the nearest neighbor search or the stratified search for the seed sub-trajectory thereby obtaining similar sub-trajectories for members other than the seed member. The sequence of steps also includes determining a seed member cohort including members with sub-trajectories similar to the seed member, based on the seed sub-trajectory, and according to the similar sub-trajectories. The sequence of steps also includes ranking one or more seed treatment strategies most likely to be efficacious for the seed member based on outcomes associated with each of the seed treatment strategies applied to the seed member cohort. The sequence of steps also includes adjusting hyper-parameters for the nearest-neighbor search or the stratified search based on comparing the one or more seed treatment strategies with sub-trajectories after the seed sub-trajectory for the seed member.

In some implementations, ranking the treatment strategies includes: (i) selecting, from the plurality of sub-trajectories, one or more treatment sub-trajectories of the one or more members that have taken a same prior treatment option as the patient member; (ii) grouping the one or more treatment sub-trajectories into a control arm (e.g., group) set of trajectories that includes sub-trajectories that continued taking the same treatment option as the same prior treatment option after an indexed event, and one or more treatment arm sets of trajectories that each include sub-trajectories that were prescribed a respective different treatment option after the indexed event; (iii) computing a control arm average treatment effect for the control arm set of trajectories based on analyzing the sub-trajectories, in the control arm set of trajectories, after the indexed event; (iv) computing a respective treatment arm average treatment effect, for each of the one or more treatment arm sets of trajectories, based on analyzing the respective sub-trajectories, in the respective treatment arm sets of trajectories, after the indexed event; and (v) predicting effects of the treatment strategies by averaging the control arm average treatment effect and the treatment arm average treatment effects.

In some implementations, ranking the treatment strategies for the patient member further includes: (i) performing a two-sided independent-two-sample t-test with unequal variance between the control arm set of trajectories and each treatment arm set of trajectories to test if the average treatment effect (ATE) of each treatment option is significantly different from the treatment option corresponding to the control arm set of trajectories, to obtain a respective p-value significant metric for each treatment arm set of trajectories; (ii) selecting one or more treatment options based on the treatment options corresponding to each treatment arm set of trajectories that have a p-value below a predetermined threshold; and (iii) selecting one or more recommended treatment options, from the one or more treatment options, that have a statistical power above a predetermined power threshold.

In some implementations, ranking the treatment strategies for the patient member includes ranking each treatment option based on statistical factors (e.g., p-value, and confidence intervals), and/or member-specific factors (e.g., costs and coverage).

In some implementations, ranking the treatment strategies for the patient member further includes: (i) constructing a confidence interval between control and treatment arms, and (ii) selecting one or more treatment options based on the treatment options corresponding to each treatment arm set of trajectories that have a confidence interval of a predetermined size which excludes the null value.

In some implementations, the method further includes, prior to predicting effects of the treatment strategies, accounting for covariate imbalances by applying either inverse treatment propensity weighting (IPTW) or doubly robust average treatment effects (DR) to the control arm average treatment effect and the treatment arm average treatment effects.

In some implementations, each event includes transactions that generate insurance claims, entries made in an Electronic Medical Record (EMR) during an interaction between a member and the healthcare system, or sensor data from a wearable device or similar devices.

In some implementations, each event is associated with a type, a code, a value, and a timestamp.

In another aspect, some implementations include a system configured to perform any of the methods described herein.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

DESCRIPTION OF IMPLEMENTATIONS

Figure 1:
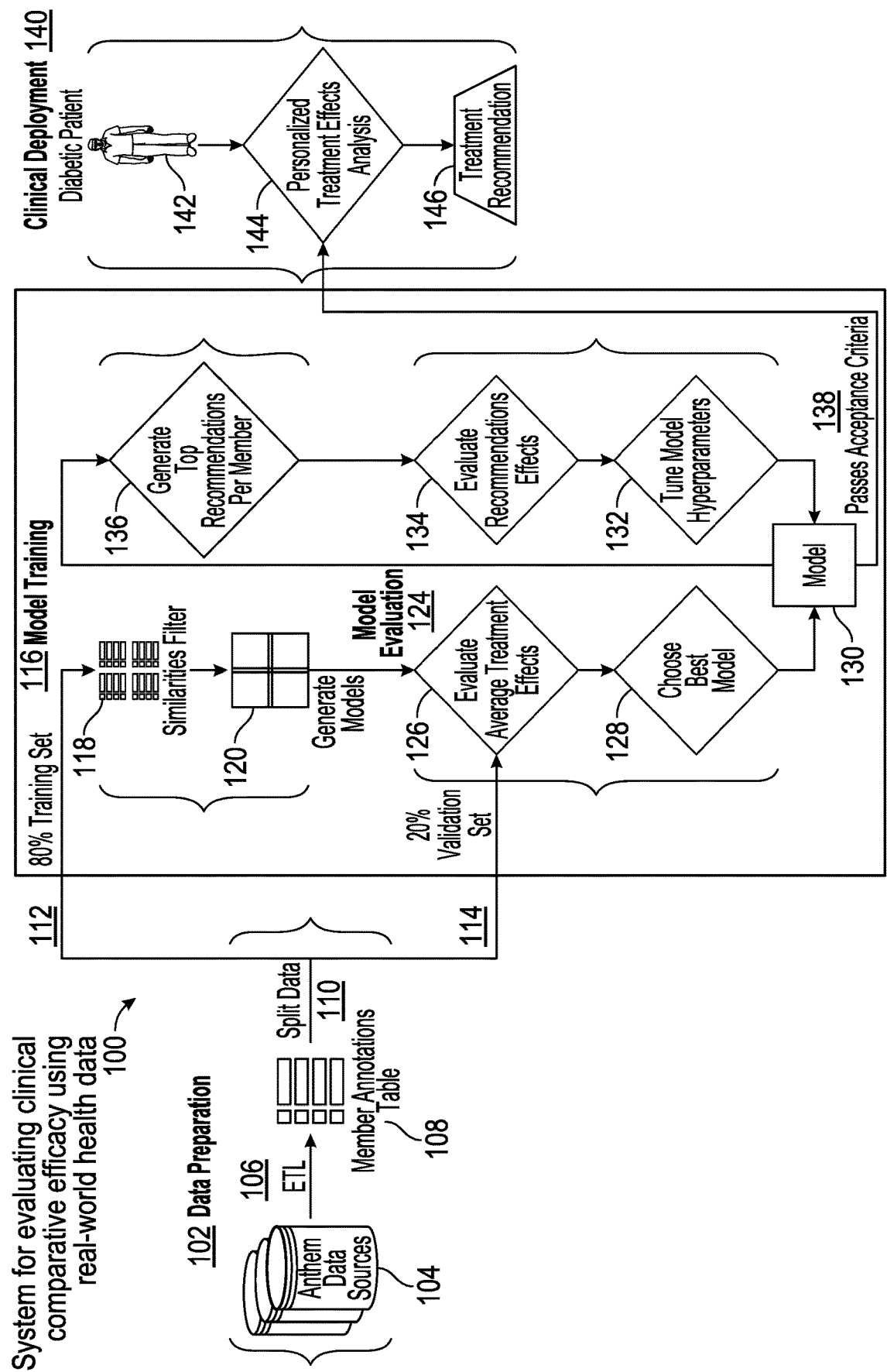
FIG. 1 is a diagram illustrating a system for evaluating clinical comparative efficacy using real-world health data, according to some implementations.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

It will also be understood that, although the terms first, second, etc. are, in some instances, used herein to describe various elements, these elements should not be limited by these terms. These terms are only used to distinguish one element from another. For example, a first electronic device could be termed a second electronic device, and, similarly, a second electronic device could be termed a first electronic device, without departing from the scope of the various described implementations. The first electronic device and the second electronic device are both electronic devices, but they are not necessarily the same electronic device.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

The techniques disclosed herein can be used to implement a treatment comparative efficacy system for a clinical setting. A system according to the invention predicts which treatment regimens will provide the highest benefit to a patient, as measured by improvements in lab results associated with a disease, according to some implementations In some implementations, the system integrates the patient's Protected Health Information (PHI) history with all of a healthcare systems' members' records. In some implementations, the system determines members who are most similar to the patient, aggregates the lab results of all treatments these members received, and predicts future lab result for each potential treatment the patient could receive. Based on these steps, the system suggests optimal treatment strategies, according to some implementations.

Some implementations use various comparative efficacy (CE) metrics to test the efficacy of a trained model. The disclosure provides an overview of embodiments of a CE system, along with specific details of the CE pipeline and metrics used to test the trained model efficacy.

A system that uses the techniques and embodiments disclosed herein can help save health care costs, and reduce insurance premiums for members of a healthcare system. Moreover, such a system helps patients receive fewer, earlier, and effective treatment options. In this way, the system can lead to fewer treatment interventions with higher success rates, thereby leading to better health for members of the healthcare system. According to some implementations, when the techniques are used in a clinical setting, the system has potential for improving the clinical experience and leading to the betterment of the healthcare system as a whole.

An example is provided to illustrate how some systems work, and to provide a motivation for other techniques disclosed herein. Suppose a patient is receiving treatment intervention for diabetes. Under some systems, the patient visits her provider to discuss her high HbA1c lab results during an annual checkup. Using the lab results and the patient's medical history, the provider gives the patient a type-2 diabetes diagnosis. The provider also prescribes metformin and schedules her next lab visit (typically 3-6 months between labs). With treatment, the patient's next lab results show no change in HbA1c. The provider prescribes an additional medication of glipizide and metformin and schedules her next lab. The patient's HbA1c results remain unchanged, so the provider prescribes an additional medication of glyclopyramide, glipizide, and metformin, and schedules her next lab. The patient's HbA1c results worsen, so the provider removes glyclopyramide from her treatment regimen and prescribes her an additional medication of insulin, glipizide, and metformin and schedules her next lab. The patient's HbA1c results fall back to her previous values so the provider trials an additional medication of glimepiride, insulin, glipizide, and metformin. Finally, the patient's HbA1c results fall to a healthier range, so the provider continues her regimen of glimepiride, insulin, glipizide, and metformin. This hypothetical example highlights issues with the existing trial-and-error approach: the patient sees her provider 6 times and has 5 lab visits outside of her annual checkup. The patient is prescribed 5 different treatments before a successful regimen is found. It is likely that the patient does not need several of her medications, and these may be causing harm in unintended ways. Meanwhile, the provider and the lab become overbooked by one patient, instead of being available to care for additional patients. At the same time, the patient deals with co-pay and/or other insurance qualms, during each provider visit and prescription filling.

Further, as described in the Background section, new drugs must first go through rigorous Randomized Controlled Trials (RCT) for FDA approval. However, real-world usages of these drugs are often not studied. Variations in dosages, frequencies, patient co-morbidities, and drug interactions are not well characterized and can lead to suboptimal to fatal responses. When a provider makes a treatment recommendation, many of these variations are not fully considered.

To address at least some of these problems, some implementations mediate by making data-driven recommendations. In some implementations, the data is sourced from a healthcare system's existing members' health records. These records are sliced into trajectories and go through filtration techniques to find member trajectories that are most similar to the patient's current trajectory. Of these similar trajectories, the system can analyze each treatment intervention that was prescribed after the trajectory's end date to predict how the patient will respond to each potential treatment option. With this, a suggested treatment regimen can be made for the patient.

FIG. 1 is an illustration of an example system 100 for evaluating clinical comparative efficacy using real-world health data, according to some implementations. Data sources 104 of a healthcare system store healthcare information on members of the healthcare system. In some implementations, an Extract-Transfer-Load (ETL) process extracts (106) necessary information from the data sources 104 to populate a member annotations table 108. In some implementations, the data stored in the annotations table 108 is split (110) or divided into a training set 112, and a validation set 114. For example, 80% of the data is used as a training set, and the rest is used for validation. A predictive model (sometimes called a recommendation system) is subsequently trained (116) and validated (124) as shown in the highlighted box. In some implementations, one or more similarities filters 118 are used to identify members with similar trajectories (or sub-trajectories) as a patient member, to generate one or more models 120. Subsequently, the one or more models 120 are validated using the validation set 114. In some implementations, the system evaluates (126) average treatment effects 126, and chooses (128) a current best model 130 from the one or more models 120. The current best model 130 is used to generate (136) top recommendations per member, according to some implementations, and the recommendations are validated or evaluated (134) for effects (on members who were prescribed the recommendations). The results of the evaluation (134) are used to fine-tune hyper-parameters of the model 130. The process is repeated until the model satisfies a threshold criterion or an acceptance criterion (e.g., the model predicts outcomes or successful treatments, above a threshold percentage, such as 95%, for a majority of members, for a majority of diseases, for a subset of members, for a subset of diseases, or similar criteria). Once the model passes the acceptance criteria, the model is deployed (140) for making recommendations in a clinical setting, according to some implementations. An example deployment is when a patient member 142 with diabetes visits his/her primary care physician (PCP), the system 100 or the trained model is used to perform personalized treatment effects analysis (144) for the patient member to make a treatment recommendation 146 for the patient member 142, according to some implementations. Further details of the various blocks in FIG. 1 are described below in references to FIGS. 2, 3, 4A, 4B, 5, and 6, according to some implementations.

Figure 2:
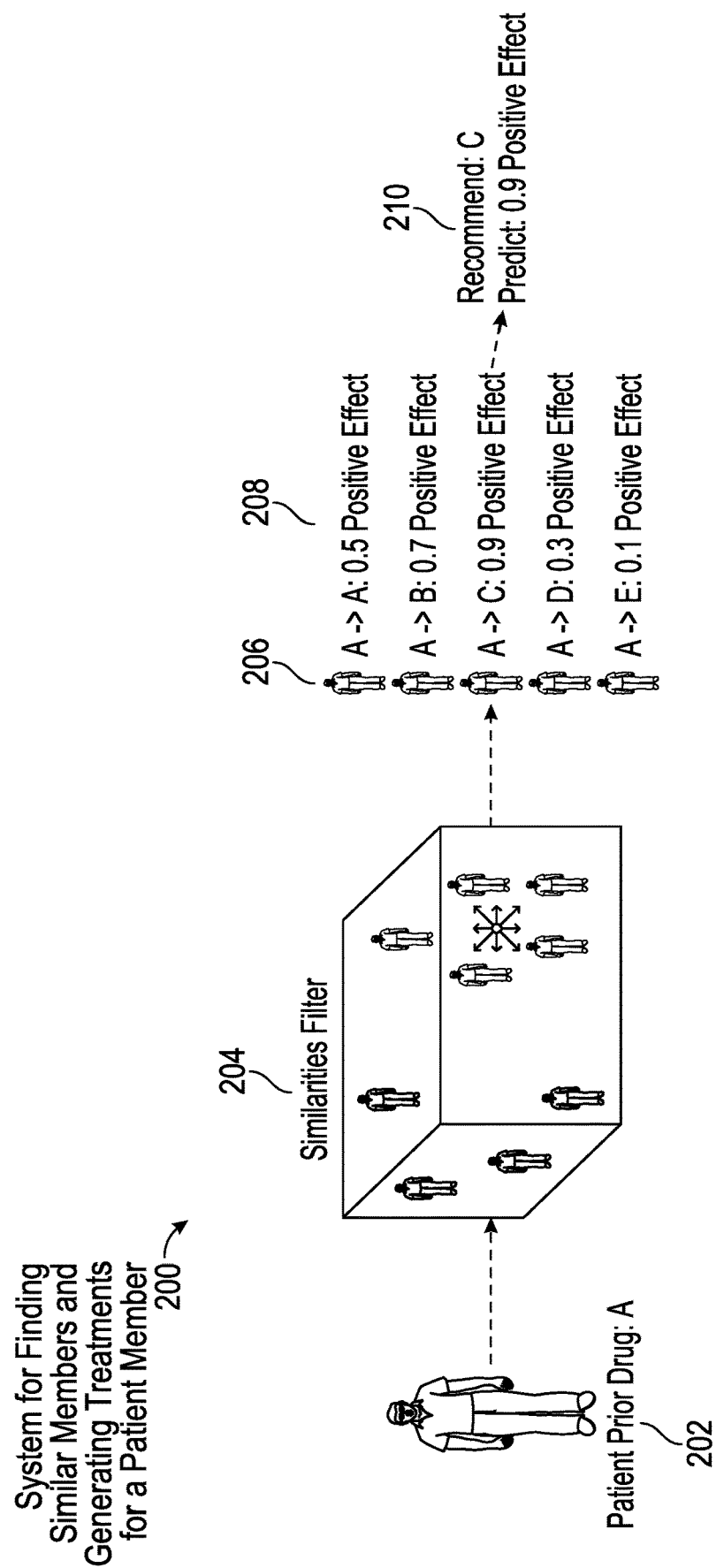
FIG. 2 is a diagram illustrating a system for finding similar members and for generating treatments for a patient member, according to some implementations.

FIG. 2 is an illustration of an example system 200 for finding similar members and generating treatments for a patient member, according to some implementations. A generic similarities 204 filter determines members 206 who are most similar to a patient based on the patient's prior drug regimen 202. The similar members' treatment results 208 are aggregated or combined to produce a recommendation 210. In the example shown, the recommendation 210 is to start drug regimen C with a predicted efficacy of 0.9. The drug regimens A, B, D, and E with lower efficacy (0.5, 0.7, 0.3, and 0.1, respectively) are disregarded. Some implementations rank the positive effects (sometimes called predicted efficacy), and provide the ranking to a provider to make a selection for prescribing a drug regimen for the patient member. Although the example shows positive effects, depending on the situation, the recommended choice can be either the highest value of predicted efficacy or the lowest value of predicted efficacy. For example, it might be more appropriate lower a particular clinical value (than raise the clinical value as the example in FIG. 2 illustrates) to make the patient member healthier.

Figure 3:
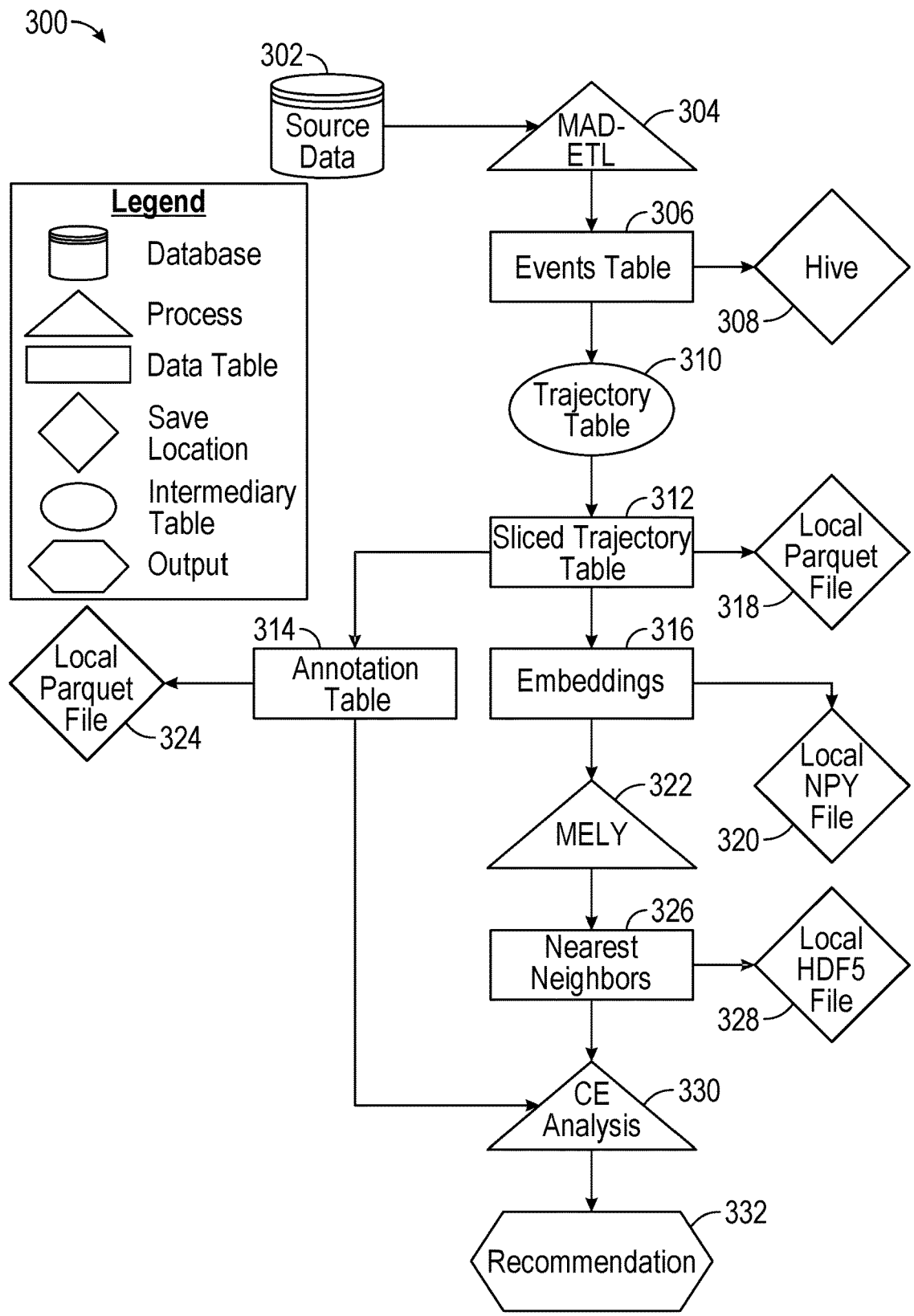
FIG. 3 is a flowchart representation of a method of determining treatment recommendations for members of a healthcare system, according to some implementations.

FIG. 3 is a flowchart of an example method 300 (sometimes called a pipeline) for generating treatment recommendations for a patient, according to some implementations. The pipeline uses data from a healthcare system's data source(s) 302 which include Electronic Health Records (EHR), claims data, and laboratory records, and generates a treatment recommendation (or a ranked set of treatment strategies or recommendations) for a patient member of the healthcare system, according to some implementations. Some implementations perform a Magnetic, Agile, Deep Extract-Transfer-Load (MAD-ETL) step (304) to generate an events table 306. Some implementations generate a trajectory table 310 based on the events table 306, and a sliced trajectory table 312 based on the trajectory table 310. Some implementations generate an annotation table 314 and embeddings 316 based on the sliced trajectory table. In some implementations, one or more algorithms (322; sometimes called Members Like You, or MELY) use the embeddings 316 to determine nearest neighbors 326. Subsequently, a comparative efficacy analysis module or process (330) analyzes the nearest neighbors 326 to generate treatment recommendations 332, according to some implementations.

In some implementations, the events table 306 is saved (or stored) to a Hive database 308 or a similar scalable database, as a source for training data and/or feature engineering. In some implementations, the annotations table 314 and/or the sliced trajectory table 312 are stored to local parquet files (or in similar file formats that support multi-dimensional data, distributed and/or parallel processing) 324 and 318, respectively. In some implementations, the embeddings 316 are stored to a local Numpy (NPY) file or in a similar binary file format and/or a high performance file format, for feature engineering and/or for training purposes. In some implementations, the nearest neighbors 326 are stored in a HDF5 or a similar hierarchical data file formats (HDF), such as BAM, and VCF, that are designed to support large, heterogeneous, and complex datasets, suitable for high dimensional data. The different file formats and file stores are used in feature engineering, for training, and/or for inferencing, according to various implementations.

Example Extract-Transfer-Load (ETL) Steps

This section describes steps for generating the sliced trajectory table 312 and/or the annotations table 314, according to some implementations.

Some implementations generate an events table 306 (e.g., a tall and narrow table with many rows and few columns) with non-unique patient IDs (PIDs) that describes a prescription, diagnosis, or procedure code along with the lab value (if applicable) for a patient. Each PID has several associated events, and therefore many rows. An example schema is shown below for illustration, according to some implementations.

Schema:

| PID | Event | Date | Code | Value | Claim Key | Days' Supply |
|-----|-------|------|------|-------|-----------|--------------|

Some implementations aggregate the events table 306 into a wide trajectory table 310 with unique PIDs that detail the time series of the patient's entire medical history. An example is shown below for illustration, according to some implementations.

| PID1 | Code1 | Code2 | Outcome_1A | Code3 | | Code4 | Outcome_1B | Code5 | ... |
|------|-------|-------|------------|-------|--|-------|------------|-------|-----|
| PID2 | Code6 | Code7 | Code | Outcome_2A | | | | | |

Given a disease and an indexed event (ex: diabetes and HbA1c lab results), some implementations generate a sliced trajectories table 312 with non-unique PIDs but with unique trajectory indexes (labelled "PID_DATE") as the key. In some implementations, the DATE label in the trajectory index stands for the end date of that trajectory window, which is the indexed event. In some implementations, each row details the member's history up to the indexed event. An example is shown below for illustration, according to some implementations.

| PID1 | PID1_Date1 | Code1 | Code2 | Outcome_1A | | | |
|------|------------|-------|-------|------------|--|--|--|
| PID1 | PID1_Date2 | Code1 | Code2 | Outcome_1A | Code3 | Code4 | Outcome_1B |
| PID1 | PID1_Date3 | Code1 | Code2 | Outcome_1A | Code3 | Code4 | Outcome_1B Code5 |
| PID2 | PID2_Date1 | Code6 | Code7 | Code8 | Outcome_2A | | |

Some implementations create an annotations table 314 describing each sliced trajectory's prior drug regimen and lab results, as well as the future subsequent drug regimen and lab results following the index event. In some implementations, other information, such as demographics and co-morbidities, are included as well for downstream member sub-population filters. An example schema is provided below for illustration, according to some implementations.

| Trajectory Index | PID | Drugs | Last Refill | Lab Prior | Lab After | Lab Prior Date | Lab After Date | Prior Drugs | Demographics | CM |
|------------------|-----|-------|-------------|-----------|-----------|----------------|----------------|-------------|--------------|----|

In the example above, CM refers to co-morbidities

Example Sliced Trajectories

When making a recommendation for a patient, in some implementations, the system compares the efficacy of all potential treatment interventions that each similar member (to a patient) has undergone. In some implementations, this is performed by measuring, for all members, change in relevant lab values before and after each new treatment regimen is prescribed (including control cases where the same treatment regimen is prescribed). Compared to finding members with similar full medical histories as the patient, it is more relevant to find slices (e.g., portions, or subsets) of member histories, called sliced trajectories, that are most similar to the patient's current trajectory. This allows the system to identify members who, at some point in the past, were similar to the current patient but are not similar to the patient today. For example, if the current patient is 40 years old, there may be a member who is currently 60 years old. The two may not be similar now, but the may have been similar when the 60 year old was 40.

Figure 4A:
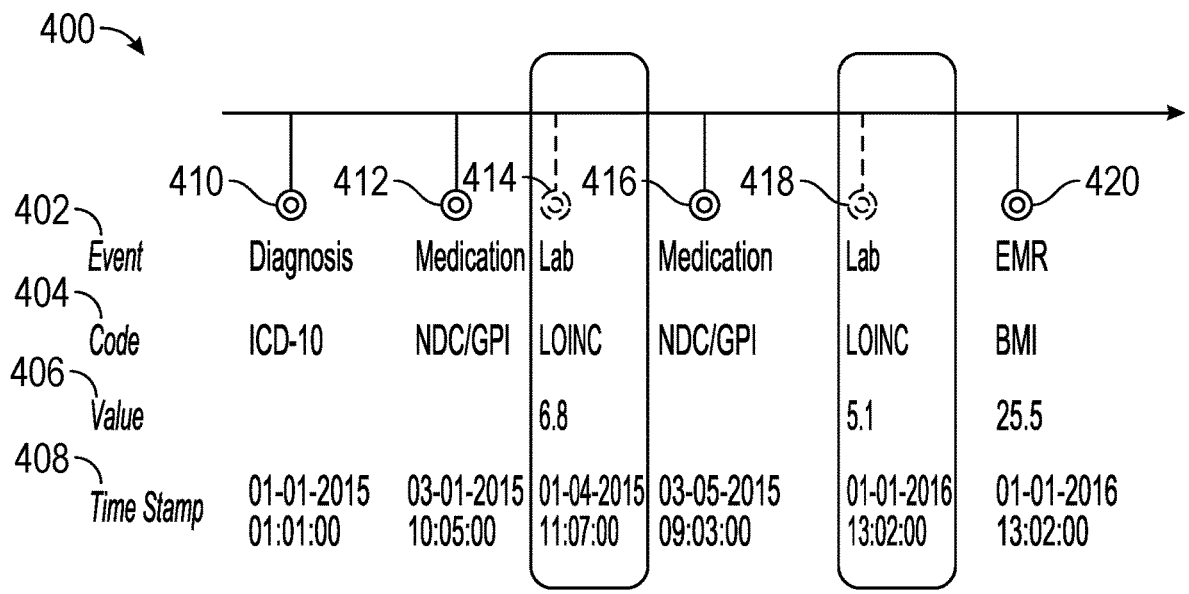
FIGS. 4A and 4B are illustrations of example healthcare trajectories, according to some implementations.
Figure 4B:
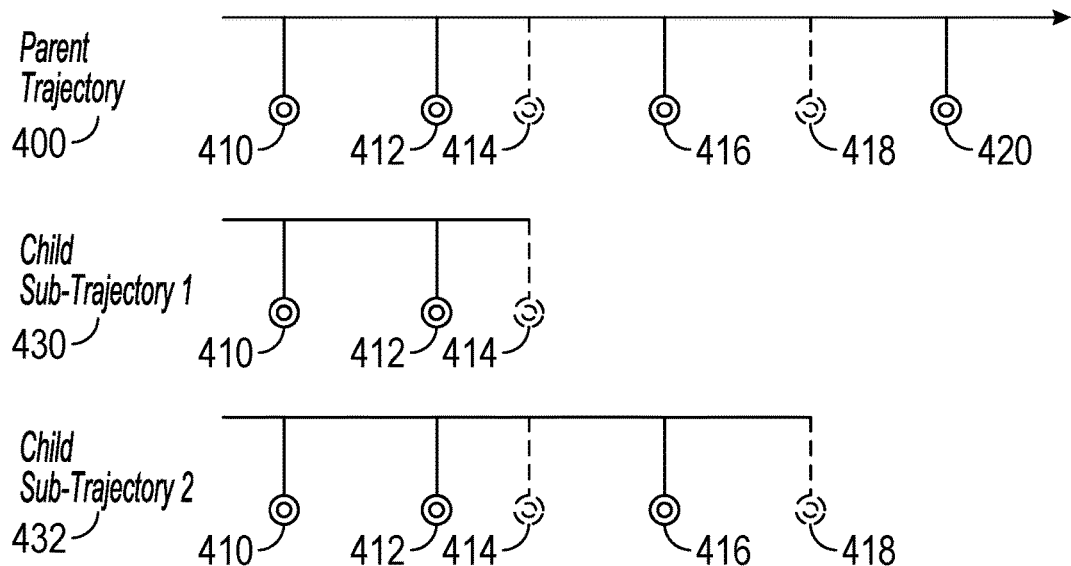

To create sliced trajectories, in some implementations, member histories are delimited on indexed events, such as lab readings (e.g., HbA1c lab readings), and/or any health value or health occurrence, whether clinical, medical, behavioral, or lifestyle, that a patient or provider may wish to improve (such as a lab value, a mental health assessment, a variation in heart rate, their body weight, etc) or avoid (such as a heart attack, being admitted to the hospital, amputation, a corrective surgery, etc. An index event may be any clinical or health data point. In some implementation, an index event may be any clinical or health data point that can be intervened upon. Intervention could be performed by a provider, a behavioral coach, an application, etc. In some implementations, each trajectory starts from the beginning of the patient's history and ends at one of the indexed events (also referred to herein as a terminal index event). In FIG. 4A, for example, a member history is split or indexed on the lab code LOINC 414, 418, and the subsequent trajectories are created. FIGS. 4A and 4B are example illustrations of generation of sliced trajectories (child sub-trajectories) from a patient's full medical history.

FIG. 4A is an example of a trajectory 400 for a patient, according to some implementations. As illustrated, each health trajectory corresponds to a respective member and represents time-ordered series of events for the respective member, and each event represents an interaction between the respective member and the healthcare system. In FIG. 4A, the events 402 include diagnosis 410, medication 412, lab 414, medication 416, lab 418, and EMR 420. The codes 404 for the events 402 include ICD-10, NDC/GPI, LOINC, NDC/GPI, LOINC, and BMI, respectively. The lab events 414 and 418, and the EMR event, correspond to values 6.8, 5.1, and 25.5, respectively, according to some implementations. Each of the events 402 include a corresponding to time stamps 408, according to some implementations.

FIG. 4B is an illustration of sub-trajectories of the trajectory 400 shown in FIG. 4A, according to some implementations. The example parent trajectory 400 includes event 410, event 412, event 414 (an index event), event 416, event 418 (an index event), and event 420. A first child sub-trajectory 430 includes events 410, 412, and 414, and terminates at the index event 414. A second child sub-trajectory 432 includes all the events in the first child sub-trajectory 430 as well as the events 416 and 418, and terminates at the index event 418. Similarly, trajectories for all members of a healthcare system are sliced into sub-trajectories, according to some implementations.

Example Annotation Table

In some implementations, an annotation table 314 provides details of each patient's trajectories used in a downstream sub-population filtering process during comparative efficacy analysis. In some implementations, this information acts as the ground truth, allowing the system to compare the predicted effects of a drug with their actual effects. In some implementations, this also allows the system to filter on demographics and specific co-morbidity profiles, allowing for more targeted treatment recommendations. Further details related to the comparative efficacy are provided below in the section on comparative efficacy pipeline, according to some implementations.

Example Embeddings

In some implementations, the system uses a large number of features to find similar members. Using more features can lead to a more complex model capable of finding more complex relationships. However, as a detriment of dimensionality, this comes with a cost of skewing similarities filters, particularly when using the k-Nearest-Neighbors technique. Some implementations perform dimensionality reduction, such as Principle Component Analysis (PCA), on the data to minimize this cost by producing lower-dimensional embeddings that are fed into machine learning models.

In some implementations, the generated sliced trajectories table 312 is horizontally appended with all diagnoses and prescription codes in a one-hot format that counts the number of occurrences of each code, producing a very wide (>100,000 columns) and very sparse table. In some implementations, this table 312 is input into a low-rank implicit matrix factorization (MF) job using Alternating Least Squares (ALS) to create an embeddings table with floating-point vector embeddings for each row.

In some implementations, the MF job is derived from an unsupervised transformation of the data. Yet, due to the co-occurrence of many interventions that patients have had as they related to a disease, one embedding value can be a combination of many related codes. For example, many patient histories would have co-occurrence of codes for mastectomy and breast reconstruction surgery as a result of breast cancer, and these are captured by one floating-point value. Therefore, one embedding can be representative of traditional clinical factors used during treatment recommendation by the provider, according to some implementations. Other embeddings can be less obvious clinical factors that may provide association to treatment outcomes. In some implementations, the system captures all of these associations to make better treatment predictions.

In some implementations, another set of embeddings can be generated from traditional clinical factors. These include patient demographics and comorbidities. They are created through one-hot encoding of these values, and act as a similarities filter to create population segments. While these are not used in the PIP pipeline, they can be useful when doing comparative efficacy analysis.

Example Similarities Search Algorithm (kNN)

In some implementations, with trajectory embeddings 316, the system finds similar member trajectories (nearest neighbors 326) using a k-Nearest-Neighbors (kNN) technique through a subsystem called MELY 322 (MEmbers Like You). In some implementations, MELY sets each trajectory into a multi-dimensional (e.g., 100 dimensions) feature space where each embedding's component value represents a coordinate on an axis of the feature space. Once fitted, each member trajectory (seed member) can be pre-computed with their k-nearest-neighbors by using the Euclidian distances between these points. In some implementations, the number of neighbors, K (e.g., an integer), is a tunable hyper-parameter.

Example Neural Network (RNN)

Figure 5:
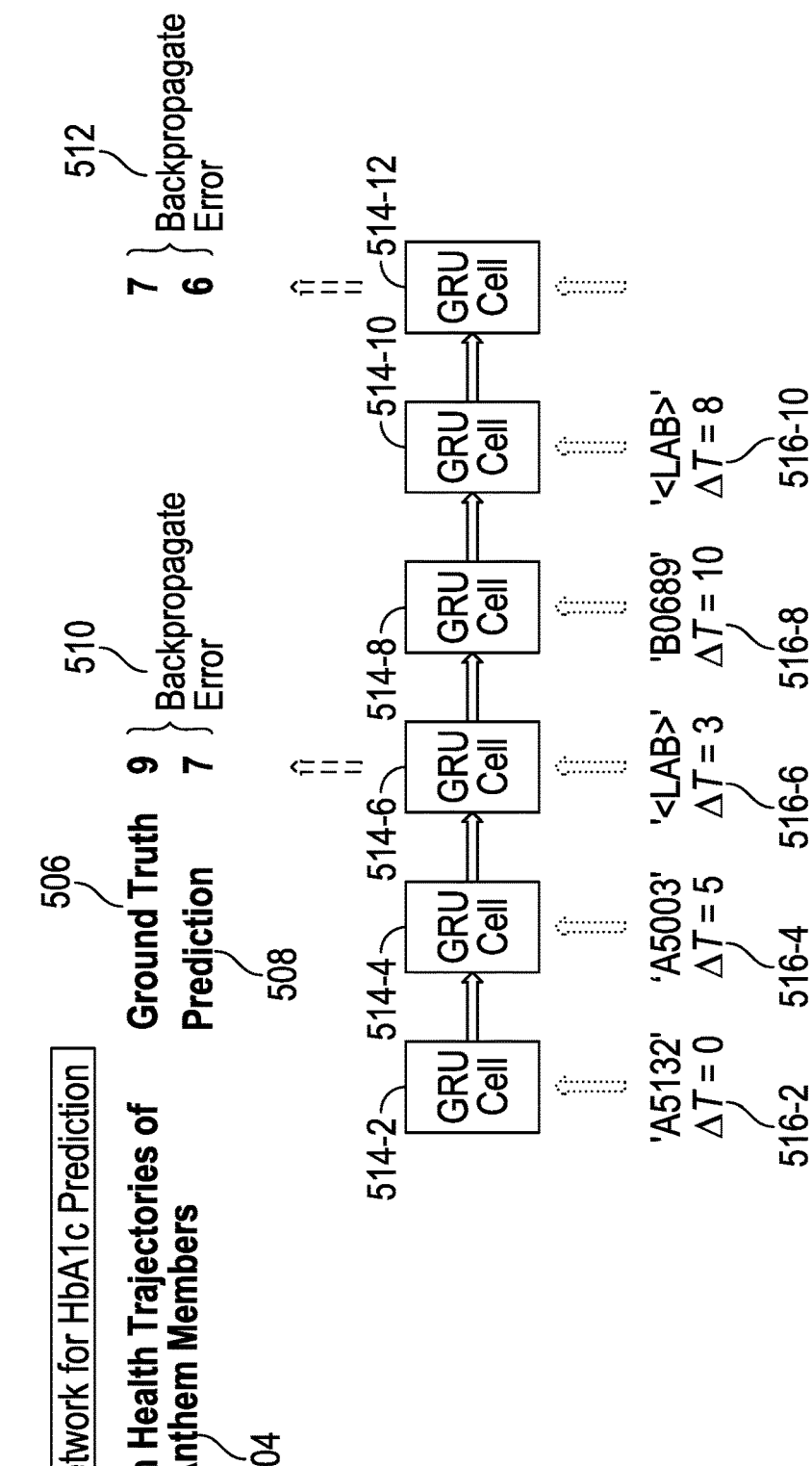
FIG. 5 is an illustration of an example recurrent neural network (RNN) for predicting lab results that uses backpropagation, according to some implementations.

Some implementations predict optimal treatment recommendations using a deep recurrent neural network (RNN), an example of which is shown in FIG. 5. The example network 500 predicts lab results and back-propagates the error, according to some implementations. More specifically, the neural network 502 is used for HbA1c prediction 502, and is trained on health trajectories of a large number of healthcare members (e.g., 4 million members). In some implementations, the RNN 500 is made up of Gated-Recurrent-Unit (GRU) cells (e.g., the cells 514-2, 514-4, 514-6, 514-8, 514-10, and 514-12), which take the raw trajectories data (e.g., the data 516-2, 516-4, 516-6, 516-8, and 516-10, respectively) as input, and learn the embeddings when training end-to-end. In the example, the raw trajectories data 516-2, 516-4, 516-6, 516-8, and 516-10, correspond to codes AS132, AS5003, LAB, B0689, and LAB, respectively, and time durations (e.g., times calculated based on time stamps) between consecutive events for the raw-trajectories data are indicated as 0, 5, 3, 10, and 8, respectively. Alternatively, some implementations use a pre-trained model (transfer learning) that use input that are pre-embedded vectors that are generated from the embeddings MF step (described above). In various implementations, the target of the neural network is set to a real number to perform a regression task, or a binned value to perform a softmax classification task. The ground truth 506 and prediction 508 values for the RNN 500 are indicated as shown. The GRU cell 514-6 predicts a value of 7 (when the ground truth value is 9), and the GRU cell 514-2 predicts a value of 7 (when the ground truth is 7), and the error values are back-propagated to the network (e.g., the back-propagations 510 and 512).

Example Comparative Efficacy Pipeline

An example comparative efficacy pipeline is described for illustration, according to some implementations. The sections that precede outlined steps that the system uses to determine members with trajectories most similar to a given patient's current trajectory. Subsequently, the data within this set of similar members are aggregated to generate a treatment recommendation for the patient, as well as a prediction for how well the treatment will affect the patient's subsequent lab values.

Referring to the example described above in the beginning of the detailed description section, in contrast to today's existing practice, here is a hypothetical story of a patient's visit to her provider. In this case, the provider is using the system according to the techniques disclosed herein. The patient goes to her provider to discuss her high HbA1c lab results during an annual checkup. Using the lab results and the patient's medical history, the provider gives the patient a type-2 diabetes diagnosis. The provider uses the system's recommendation for treating the patient with glimepiride and predicts her HbA1c results will fall by 2.4. The provider then schedules the patient's next lab visit. The patient's next lab visit shows that the treatment is working, and her lab results fell close to the prediction and within healthy range. The patient continues this treatment regimen of 1 drug. As such, with the system's recommendation, the patient's treatment required less provider and lab visits, less drug trials, fewer drugs as part of her final regimen, and the provider was able to see more patients. In this way, the system benefits the healthcare system as a whole.

To enable the comparative efficacy pipeline to make comparisons between its predictions of drug interventions and their actual effect in members, some implementations obtain (or generate) a ground truth table. In some implementations, the annotation table 314 provides this ground truth. In some implementations, first, filtering techniques segment the annotation table 314 into sub-populations. In some implementations, statistical analyses are then performed to get the Average Treatment Effect (ATE) of the intervention among the population segment, allowing the system to make predictions on the drug effects for a given patient. In some implementations, the system subsequently makes a recommendation from among the top recommended drugs for a patient, and then cross-references to see if any patient within a validation set took one of the recommended drugs. In some implementations, the system validates how the model is performing when compared to other non-machine-learning baseline filtering techniques. Some implementations measure accuracy and efficacy metrics in the machine learning process and compares those values to other validation techniques, thereby improving the model over time. Some implementations use this validation approach to determine if the model has achieved a threshold accuracy level (e.g., 95% or above).

Example Filtering

In some implementations, the system uses the kNN technique as a similarities filter to identify members that are similar to a given patient. Some implementations use simpler similarities filters to validate how well the system performs compared to non-machine-learning methods. In the event that the model used by the system is inaccurate, incomplete, or underspecified for a given member, some implementations use fallback filtering techniques. In some implementations, additional baseline filtering techniques are also used to compare the models' performances to simple filtering methods. Some implementations employ the following fallback and baseline filters, based on the annotation table 314, to create sub-population segments, which are then used to judge model efficacy:

Prior Drugs Filter (baseline)—The annotation table 314 is filtered on member trajectories that have taken the same prior drugs only.

Prior Labs Filter (baseline)—The annotation table 314 is filtered on member trajectories that have taken the same drugs and those who fall into binned values for their prior lab results. This is because members with high values are expected to have a disproportionate change in future lab results than members with low values. For diabetes, for example, the prior lab bin size is set to 1.0 HbA1c values.

Demographic Filter (baseline)—The annotation table 314 is filtered on member trajectories that have taken the same drugs and who fall into binned age values and who are of the same gender.

Co-morbidities Filter (baseline)—The annotation table 314 is filtered on member trajectories that are presenting the same unique set of co-morbidities relevant to the disease.

Stats Model without Demographics or Co-morbidities Filter (fallback)—The annotation table 314 is filtered on member trajectories that have taken the same drugs and who fall into binned prior lab values. Additionally, statistical significance testing and power thresholding is performed (described below in following sections).

Full Stats Model Filter (fallback)—The annotation table 314 is filtered using one or more filtering techniques described above, as well as filtering on statistical power thresholding.

In some implementations, the above filtered population segments are compared with the system's kNN similarities filter. In the case of kNN technique, once a set of similar members trajectories are found for the patient, the trajectories are first filtered to only include those members that have used the same prior drugs as the patient. This ensures that the a priori condition on prior drugs is met, and the recommendation being made is based on conditions relevant to the patient's current trajectory.

For the kNN and fallback filtering groups with statistical power thresholding, the comparative efficacy pipeline will then analyze each unique treatment regimen from these filtered subsets of similar members. For each unique regimen, some implementations perform statistical analysis to measure the predicted effect along with a power metric. In some implementations, this provides a cutoff when determining which treatment option will provide the highest predicted benefit to the patient so that a recommendation can be made.

Example Prediction

In some implementations, each trajectory within the set of similar trajectories who have taken the same prior drug regimen is grouped into either control or treatment arms. A control arm is defined as those trajectories that continued taking the same drug regimen as the prior regimen after the indexed event (typically a lab result). In contrast, the treatment arms are defined as trajectories that were prescribed one of several new treatment regimens after the indexed event. Each new treatment regimen is grouped together as a separate treatment arm. In some implementations, the average treatment effect (ATE) of each option (control and treatments) is computed from the actual effects observed from the trajectories in each arm. This prediction value is the average (expected) change in lab readings: prediction=ATE=$(1/n)\Sigma$(actual_effect). In some implementations, this predicted effect of each drug is compared to the actual effect that drug had on the patients within the validation set (as discussed in the model validation section).

Example Recommendation

In some implementations, after generating one control arm and multiple treatment arms, statistical analyses is performed to create recommendations. In some implementations, when the population variance cannot be calculated for each group (only the sample variance can be calculated), the arms are conservatively assumed to have non-equal variance. Some implementations perform a two-sided independent-two-sample t-test with unequal variance between the control arm and each treatment arm to test if the average treatment effect (ATE) of each treatment option is significantly different from the control. In some implementations, the result gives a p-value significance metric for each treatment arm compared to the control. In some implementations, significant ATE are associated with p-values <0.05.

In this way, in some implementations, the system generates a set of best drug options to recommend, and worst drugs that should be avoided. In some implementations, each significant drug (p<0.05) is predicted to have either a better effect or a worse effect. In some implementations, a power metric (e.g., a function of mean effect, significance threshold, and sample size in each arm) further thresholds these drugs. In some implementations, this provides confidence that the predicted effect size is close to the true effect size. In some implementations, on this basis, the system recommends drugs that have the highest mean effect in this group. Additionally, in some implementations, the system notifies the provider which drugs to avoid, as they are predicted to provide the worst effects.

Figure 6:
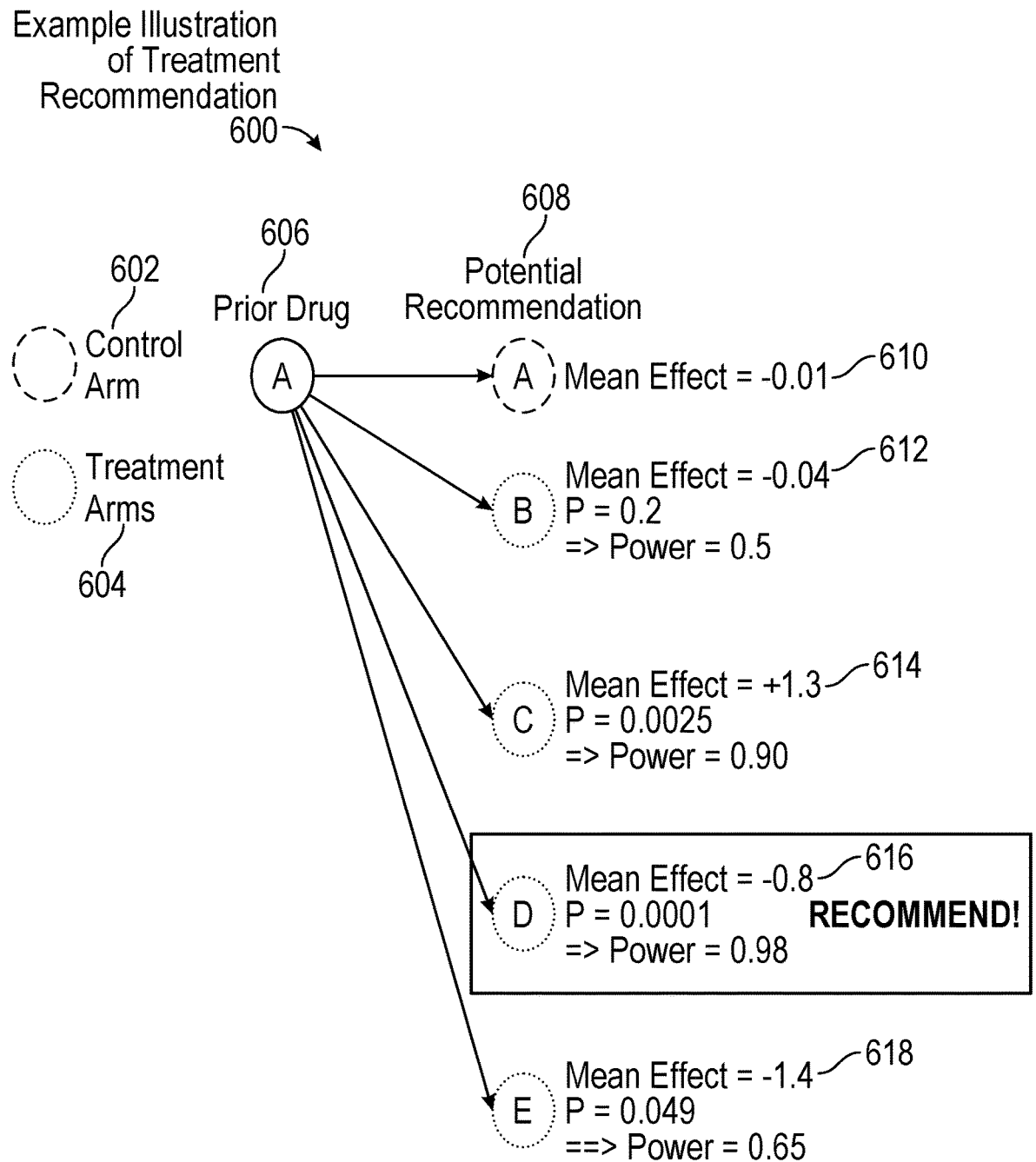
FIG. 6 is an illustration of an example of treatment recommendation, according to some implementations.

FIG. 6 is an example illustration of treatment recommendation, according to some implementations. Various potential recommendations 608 are shown. The control arm (green) 602 shows the predicted effect 610 of the patient continuing on the medication. If all other treatment arms (purple) 604 show poor results (e.g., mean effect 614 for drug C is +1.3), then the recommendation is to stick with Drug A (prior drug 606). However, some treatment arms demonstrate good mean effects (e.g., Drugs B, D, E, with respective mean effects 612, 616, and 618, with values −0.04, −0.8, and −1.4, respectively). Of these, only Drugs D and E are considered because they have a p-value<0.05. Additionally, Drug D demonstrates statistical power (value of 0.98) above the 0.8 threshold, so even though it doesn't have the best mean effect, the system is confident that the predicted effect on the patient is close to −0.8. Therefore, in some implementations, drug D is recommended.

Example Model Validation

In some implementations, the model's accuracy and efficacy are validated before deploying the system into the clinical setting. In some implementations, the model is used for specific diseases, specific population segments, prior drug conditions, and/or for recommending drugs for specific members.

In some implementations, to validate the model, trajectories from the annotations table 314 are randomly split into training (80% of data) and validation (20% of data) sets. In some implementations, the training set is used to generate ATE (as described above), which is the prediction for how an intervention will perform on a patient given prior conditions. In some implementations, the test set is used to measure the accuracy of these predictions using the root-mean-squared-error (RMSE) metric. For each trajectory in the validation set, some implementations start with an assumption regarding what the predicted effect should be dependent on (e.g., prior conditions, such as the prior drug used). Some implementations measure the error from this prediction and the trajectory's actual change in lab value.

In some implementations, the accuracy is measured for all treatment interventions taken by the test population, which include drugs with both good and bad effects. Additionally, to measure the system's efficacy as a recommender system, some implementations use the mean change in outcomes in the recommended population. Some implementations filter the test set trajectories to only include those that took one of the treatment interventions that the system recommended, given the trajectory's prior conditions. Some implementations compare the mean effect size of the treatment for this population subset to the predicted effect of this subset, to determine the model's overall efficacy.

Examples of Methods for Evaluating Clinical Comparative Efficacy

This section describes example methods of evaluating clinical comparative efficacy using real-world health data, according to some implementations. The method is executed at a computing device coupled to one or more memory units each operable to store at least one program. One or more servers having at least one processor communicatively coupled to the one or more memory units, in which the at least one program, when executed by the at least one processor, causes the at least one processor to perform the method.

The method includes obtaining health trajectories for members of a healthcare system. Each health trajectory corresponds to a respective member and represents time-ordered series of events for the respective member, and each event represents an interaction between the respective member and the healthcare system. For example, as described above in reference to FIG. 1, the health trajectories are obtained from one or more data sources (e.g., the data sources 104), according to some implementations.

The method also includes identifying index events in the health trajectories for the members. An index event is any clinical or health data point. Examples of index events are events, such as lab events, drug prescriptions, diagnoses like diabetes, heart rate, etc.

The method also includes segmenting the health trajectories with index events into a plurality of sub-trajectories such that each sub-trajectory ends at a different index event. In various implementations, sub-trajectories may begin either at the first event on record for the member or the first event within a certain look-back period prior to the index event (e.g., 6 months prior to the index event), and each parent trajectory will have as many child sub-trajectories defined by index events. For example, as described above in reference to FIGS. 4A and 4B, the health trajectories are segmented into child sub-trajectories with one or more index events. The last index event is sometimes called the terminal index event.

The method also includes generating a digital fingerprint for each or representative of each sub-trajectory by either (i) generating a raw data vector from raw trajectories data representing the health trajectories, or (ii) applying representation learning to generate an embedding vector. In some implementations, the digital fingerprints are represented as raw trajectories data, and generating the raw data vector includes converting a series of real clinical variables into a real vector format. For example, some implementations build a model using one or more clinical variables (e.g., 'current medication', and 'age', and 'sex'). The string variable (e.g., 'current medication') is mapped to an integer representing the specific value present (e.g., Drug_A is mapped to the value 1, Drug_B is mapped to the value 2, and Metformin is mapped to the value 3). A continuous variable is represented as it is (e.g., 65). Boolean variables (e.g., sex) are represented in binary (e.g., where sex is 'male' is mapped to 1, and so on). So, if a particular example had the respective values of ('metformin', 65, and F), the corresponding raw data vector is represented as [3,65,0]. In some implementations, representation learning uses an optimization function to convert raw data vectors to vectors of floating point numbers of arbitrary dimensionality. Some implementations use different ways to input variables. For example, raw values (e.g., 0.65 or age is 65) may be input. Some implementations build a model that takes as input raw data. In some implementations, all values are represented in a vector. Some implementations input raw data vector to a representation learning algorithm to generate new vector. Some implementations learn functions (e.g., non-linear transformation functions) to transform inputs to different dimensions. In some implementations, raw variables are only used to generate embedding vectors, and are not input to the system in any other manner. Example generation of raw data vectors from raw trajectories data representing the health trajectories, and/or applying representation learning to generate the embedding vector are described above in reference to FIG. 3, according to some implementations.

The method also includes identifying one or more sub-trajectories that are similar to a patient sub-trajectory (either a current sub-trajectory or a historical sub-trajectory) by either (i) performing a stratified search to select the one or more sub-trajectories from the plurality of sub-trajectories based on one or more stratifying criteria, or (ii) performing a nearest-neighbor search on the embedding vectors of the members. The patient sub-trajectory corresponds to a patient member of the healthcare system. In some implementations, the method to select stratifying variables, similar neighbors, number of nearest neighbors (k), and/or distance to similar neighbors are hyper-parameters that are determined via cross-validation. Example similarities filter and performance of nearest-neighbor search are described above in reference to FIGS. 1, 2, and 3, according to some implementations.

The method also includes ranking or identifying treatment strategies that are most likely to be efficacious for the patient member based on outcomes (e.g., real-world historical outcomes) associated with each of the treatment strategies, according to the one or more sub-trajectories. In some implementations, similar members are identified using similar digital fingerprints, and the treatment strategies are ranked based on strategies that are most likely to be efficacious for the patient member based on outcomes associated with each of the treatment strategies for the similar members, according to the one or more sub-trajectories. Example treatment recommendation methods and/or ranking techniques are described above in reference to FIGS. 2, 3, and 6, according to some implementations.

In some implementations, the method includes generating the embedding vectors includes mapping raw data encodings, of distinct member features for the members, that include demographic, clinical data, and laboratory data.

In some implementations, the method includes applying representation learning algorithm includes performing matrix factorization to the raw trajectories data to convert the raw trajectories data to a vector of floating point numbers. Performing the matrix factorization includes: generating a sparse matrix, wherein each row of the sparse matrix represents a respective sub-trajectory, and each column represents a respective claim code representing a respective event; and factorizing the sparse matrix using Alternating Least Squares (ALS) to obtain a first factor that includes trajectory embedding matrix and a second factor that includes code embedding matrix. One axis of the trajectory embedding matrix correspond to floating-point vector representations of the plurality of sub-trajectories, and one axis of the code embedding matrix correspond to floating-point representations of claim codes.

In some implementations, applying representation learning comprises, performing a sequence of steps for each sub-trajectory of the plurality of sub-trajectories. The sequence of steps includes: obtaining code embeddings corresponding to claim codes representing events in the sub-trajectory; inputting the code embeddings to a trained sequence model (e.g., a recurrent neural network (RNN), such as the network described above in reference to FIG. 5, or a transformer attention network for concurrent processing of the codes) to obtain hidden states for different layers for a terminal index event (e.g., final index event) for the sub-trajectory; and combining the hidden states (e.g., either by conjugation, or by computing the weighted average) for the different layers to obtain the embedding vectors for the sub-trajectory. In some implementations, the codes are treated as tokens and embedded into vectors of floating-point numbers. In some implementations, input time interval between codes are also input to the model. This time interval may be input as a real number, as a binned value, or as an embedded vector of the binned value. Alternatively, instead of passing tokens one at a time, codes within a fixed time window may be aggregated and passed to the network. Additional inputs may include lab values at previous visits, co-morbidity scores at previous visits, etc.

In some implementations, obtaining the code embeddings includes generating the code embeddings using a code embedding model selected from the group consisting of: a matrix-factorization model, a skip-gram model, and a continuous-bag-of-words model. In some implementations, the trained sequence model is trained on the health trajectories with a target selected from the group consisting of: a next code for a predetermined health trajectory; a real number or a set of real numbers which reflects overall health of a predetermined member or a set of members; a real number representing a lab value for a predetermined lab event or a measured value for a predetermined EMR event; and a presence of a predetermined code within a specified time window (e.g., a heart attack within a one-year window). In some implementations, the next code for the predetermined health trajectory corresponds to a language modeling objective, and the predetermined health trajectory is chosen randomly from the health trajectories. This may include, for example, selecting a health trajectory or a portion thereof, and predicting the next code (e.g., a next clinical visit, a clinical code, or a lab code) given the rest of the trajectory or sub-trajectories of the health trajectory). In some implementations, the real number or a set of real numbers correspond to co-morbidity scores or aggregated health index scores. When a real number (or a set of real numbers) is the target for neural network training, the modeling objective may be either treated as a regression task to output the real value, or a softmax classification task which outputs the bin in which the real number belongs. To explain further, a member or a group of members is randomly selected, and an overall health is predicted, and validated against the actual overall health.

In some implementations, performing the nearest-neighbor search is performed using k-Nearest Neighbors (k-NN) and includes hyper-parameter tuning for number of nearest neighbors and distance to similar neighbors. Example hyper-parameter tuning and/or model validation are described above in reference to FIG. 1, according to some implementations.

In some implementations, the stratifying criteria is selected from the group consisting of: use of same prior drugs as the patient member; use of same prior drugs and having similar prior lab results as the patient member; use of same prior drugs and having similar demography as the patient member; and present same set of co-morbidities relevant to a disease.

In some implementations, the method further includes, prior to identifying the one or more sub-trajectories, tuning hyper-parameters for the nearest-neighbor search or the stratified search by performing a sequence of steps. The sequence of steps includes selecting a seed member from the members of the healthcare system. The sequence of steps also includes identifying a seed sub-trajectory from the plurality of sub-trajectories, wherein the seed sub-trajectory corresponds to the seed member, and the seed sub-trajectory is not the most recent sub-trajectory for the seed member. The sequence of steps also includes performing either the nearest neighbor search or the stratified search for the seed sub-trajectory thereby obtaining similar sub-trajectories for members other than the seed member. The sequence of steps also includes determining a seed member cohort including members with sub-trajectories similar to the seed member, based on the seed sub-trajectory, and according to the similar sub-trajectories. The sequence of steps also includes selecting one or more seed treatment strategies most likely to be efficacious for the seed member based on outcomes associated with each of the seed treatment strategies applied to the seed member cohort. The sequence of steps also includes adjusting hyper-parameters for the nearest-neighbor search parameters (e.g., number of nearest neighbors k, or distance to similar neighbors) or the stratified search (e.g., method to select stratifying variables) based on comparing the one or more seed treatment strategies with sub-trajectories after the seed sub-trajectory for the seed member. The performance under the different hyperparameter scenarios is evaluated and the hyperparameter values that optimizes performance on a given metric are chosen.

In some implementations, ranking the treatment strategies includes: (i) selecting, from the plurality of sub-trajectories, one or more treatment sub-trajectories of the one or more members that have taken a same prior treatment option (e.g., a drug regimen) as the patient member; (ii) grouping the one or more treatment sub-trajectories into a control arm set of trajectories that includes sub-trajectories that continued taking the same treatment option as the same prior treatment option after an indexed event (e.g., a lab result), and one or more treatment arm sets of trajectories that each include sub-trajectories that were prescribed a respective different treatment option after the indexed event; (iii) computing a control arm average treatment effect for the control arm set of trajectories based on analyzing the sub-trajectories (e.g., changes in lab results), in the control arm set of trajectories, after the indexed event; (iv) computing a respective treatment arm average treatment effect, for each of the one or more treatment arm sets of trajectories, based on analyzing the respective sub-trajectories (e.g., changes in lab results), in the respective treatment arm sets of trajectories, after the indexed event; and (v) predicting effects of the treatment strategies by averaging the control arm average treatment effect and the treatment arm average treatment effects.

In some implementations, ranking the treatment strategies for the patient member further includes: (i) performing a two-sided independent-two-sample t-test with unequal variance between the control arm set of trajectories and each treatment arm set of trajectories to test if the average treatment effect (ATE) of each treatment option is significantly different from the treatment option corresponding to the control arm set of trajectories, to obtain a respective p-value significant metric for each treatment arm set of trajectories; (ii) selecting one or more treatment options based on the treatment options corresponding to each treatment arm set of trajectories that have a p-value below a predetermined threshold (e.g., p<0.05); and (iii) selecting one or more recommended treatment options, from the one or more treatment options, that have a statistical power above a predetermined power threshold (e.g., 0.8). In some implementations, power metric is a function of mean effect, significance threshold, and sample size in each arm. The metric is used to calculate a confidence level that the predicted effect size is close to true effect size.

In some implementations, the method further includes, prior to predicting effects of the treatment strategies, accounting for covariate imbalances by applying either inverse treatment propensity weighting (IPTW) or doubly robust average treatment effects (DR) to the control arm average treatment effect and the treatment arm average treatment effects. When estimating the average treatment effect from observational data, certain covariate imbalances in the observed outcomes may exist. In some implementations, statistical techniques are used to overcome covariate imbalances inherent in the training data. Inverse treatment propensity weighting (IPTW) involves reweighting measurement averages based on each individual's inverse of the probability of treatment. The doubly robust average treatment effects (DR) method combines IPTW approach with regression modeling of counterfactuals.

In some implementations, each event includes transactions that generate insurance claims (e.g., diagnosis, drug prescriptions, medical procedures, lab measurements), entries made in an Electronic Medical Record (EMR) during an interaction between a member and the healthcare system, or sensor data from a wearable device or similar devices.

In some implementations, each event is associated with a type (e.g., a type description, such as diagnosis event or procedure event), a code (e.g., ICD-10 code for diagnosis events or HCPCS code for procedure events), a value (e.g., blood pressure for an EMR event or measured lab value for a lab event), and a timestamp (e.g., date and/or time when the event occurred).

In some implementations, the method further includes administering at least one of the ranked or identified treatment strategies to the patient member.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A method of evaluating clinical comparative efficacy using real-world health data, the method comprising:
at a computing device:
obtaining health trajectories for members of a healthcare system, wherein each health trajectory corresponds to a respective member and represents a time-ordered series of events for the respective member, and each event represents an interaction between the respective member and the healthcare system;
identifying index events in the health trajectories for the members, wherein an index event is any clinical or health data point;
segmenting the health trajectories with index events into a plurality of sub-trajectories such that each sub-trajectory ends at a different index event;
generating a digital fingerprint for each sub-trajectory by applying representation learning to generate an embedding vector, including training a code embedding machine learning model using at least a portion of the plurality of sub-trajectories to generate embedding vectors, with a target selected from one of:
a next code for a predetermined health trajectory;
a real number or a set of real numbers which reflects overall health of a predetermined member or a set of members;
a real number representing a lab value for a predetermined lab event or a measured value for a predetermined EMR event; and
a presence of a predetermined code within a specified time window;
identifying one or more sub-trajectories that are similar to a patient sub-trajectory by performing a nearest-neighbor search on the embedding vectors of the members, wherein the patient sub-trajectory corresponds to a patient member of the healthcare system, wherein identifying the one or more sub-trajectories comprises:
selecting, from the plurality of sub-trajectories, one or more treatment sub-trajectories of the members that have taken a same prior treatment option as the patient member;
grouping the one or more treatment sub-trajectories into a control arm set of trajectories that includes sub-trajectories that continued taking the same treatment option as the same prior treatment option after an indexed event, and one or more treatment arm sets of trajectories that each include sub-trajectories that were prescribed a respective different treatment option after the indexed event;
computing a control arm average treatment effect for the control arm set of trajectories based on analyzing the sub-trajectories, in the control arm set of trajectories, after the indexed event;
computing a respective treatment arm average treatment effect, for each of the one or more treatment arm sets of trajectories, based on analyzing the respective sub-trajectories, in the respective treatment arm sets of trajectories, after the indexed event; and
predicting effects of the treatment strategies by averaging the control arm average treatment effect and the treatment arm average treatment effects; and
identifying treatment strategies that are most likely to be efficacious for the patient member based on outcomes associated with each of the treatment strategies, according to the one or more sub-trajectories,
wherein applying representation learning comprises:
obtaining code embeddings corresponding to claim codes representing events in a sub-trajectory;
inputting the code embeddings to a recurrent neural network (RNN) to obtain hidden states for different layers for a terminal index event, wherein the RNN back-propagates error while learning embeddings during training; and
combining the hidden states for different layers of the RNN to obtain the embedding vectors for the sub-trajectory.

2. The method of claim 1, wherein generating the digital fingerprint includes mapping raw data encodings of distinct member features for the members that includes demographic data, clinical data, and laboratory data.

3. The method of claim 1, wherein obtaining the code embeddings comprises generating the code embeddings using a code embedding model selected from the group consisting of: a matrix-factorization model, a skip-gram model, and a continuous-bag-of-words model.

4. The method of claim 1, wherein performing the nearest-neighbor search is performed using k-Nearest Neighbors (k-NN) and includes hyper-parameter tuning for number of nearest neighbors and distance to similar neighbors.

5. The method of claim 1, wherein identifying the one or more sub-trajectories further comprises:
performing a two-sided independent-two-sample t-test with unequal variance between the control arm set of trajectories and each treatment arm set of trajectories to test if the average treatment effect (ATE) of each treatment option is significantly different from the treatment option corresponding to the control arm set of trajectories, to obtain a respective p-value significant metric for each treatment arm set of trajectories;
selecting one or more treatment options based on the treatment options corresponding to each treatment arm set of trajectories that have a p-value below a predetermined threshold; and
selecting one or more recommended treatment options, from the one or more treatment options, that have a statistical power above a predetermined power threshold.

6. The method of claim 1, further comprising:
prior to predicting effects of the treatment strategies, accounting for covariate imbalances by applying either inverse treatment propensity weighting (IPTW) or doubly robust average treatment effects to the control arm average treatment effect and the treatment arm average treatment effects.

7. The method of claim 1, wherein each event includes transactions that generate insurance claims, entries made in an Electronic Medical Record (EMR) during an interaction between a member and the healthcare system, or sensor data from a wearable device or similar devices.

8. The method of claim 1, wherein each event is associated with a type, a code, a value, and a timestamp.

9. The method of claim 1, further comprising:
administering at least one of the identified treatment strategies to the patient member.

10. A system for evaluating clinical comparative efficacy using real-world health data, comprising:
one or more processors;
memory; and
one or more programs stored in the memory, wherein the one or more programs are configured for execution by the one or more processors and include instructions for:

obtaining health trajectories for members of a healthcare system, wherein each health trajectory corresponds to a respective member and represents a time-ordered series of events for the respective member, and each event represents an interaction between the respective member and the healthcare system;

identifying index events in the health trajectories for the members, wherein an index event is any clinical or health data point;

segmenting the health trajectories with index events into a plurality of sub-trajectories such that each sub-trajectory ends at a different index event;

generating a digital fingerprint for each sub-trajectory by applying representation learning to generate an embedding vector, including training a code embedding machine learning model using at least a portion of the plurality of sub-trajectories to generate embedding vectors;

identifying one or more sub-trajectories that are similar to a patient sub-trajectory by performing a nearest-neighbor search on the embedding vectors of the members, wherein the patient sub-trajectory corresponds to a patient member of the healthcare system, wherein identifying the one or more sub-trajectories comprises:

selecting, from the plurality of sub-trajectories, one or more treatment sub-trajectories of the members that have taken a same prior treatment option as the patient member;

grouping the one or more treatment sub-trajectories into a control arm set of trajectories that includes sub-trajectories that continued taking the same treatment option as the same prior treatment option after an indexed event, and one or more treatment arm sets of trajectories that each include sub-trajectories that were prescribed a respective different treatment option after the indexed event;

computing a control arm average treatment effect for the control arm set of trajectories based on analyzing the sub-trajectories, in the control arm set of trajectories, after the indexed event;

computing a respective treatment arm average treatment effect, for each of the one or more treatment arm sets of trajectories, based on analyzing the respective sub-trajectories, in the respective treatment arm sets of trajectories, after the indexed event; and predicting effects of the treatment strategies by averaging the control arm average treatment effect and the treatment arm average treatment effects; and identifying treatment strategies that are most likely to be efficacious for the patient member based on outcomes associated with each of the treatment strategies, according to the one or more sub-trajectories, wherein applying representation learning comprises:

obtaining code embeddings corresponding to claim codes representing events in a sub-trajectory;

inputting the code embeddings to a recurrent neural network (RNN) to obtain hidden states for different layers for a terminal index event, wherein the RNN back-propagates error while learning embeddings during training; and combining the hidden states for different layers of the RNN to obtain the embedding vectors for the sub-trajectory.

11. The system of claim 10, wherein generating the digital fingerprint includes mapping raw data encodings of distinct member features for the members that includes demographic data, clinical data, and laboratory data.

12. The system of claim 10, wherein obtaining the code embeddings comprises generating the code embeddings using a code embedding model selected from the group consisting of: a matrix-factorization model, a skip-gram model, and a continuous-bag-of-words model.

13. The system of claim 10, wherein performing the nearest-neighbor search is performed using k-Nearest Neighbors (k-NN) and includes hyper-parameter tuning for number of nearest neighbors and distance to similar neighbors.

14. The system of claim 10, wherein identifying the one or more sub-trajectories further comprises:

performing a two-sided independent-two-sample t-test with unequal variance between the control arm set of trajectories and each treatment arm set of trajectories to test if the average treatment effect (ATE) of each treatment option is significantly different from the treatment option corresponding to the control arm set of trajectories, to obtain a respective p-value significant metric for each treatment arm set of trajectories;

selecting one or more treatment options based on the treatment options corresponding to each treatment arm set of trajectories that have a p-value below a predetermined threshold; and selecting one or more recommended treatment options, from the one or more treatment options, that have a statistical power above a predetermined power threshold.

15. The system of claim 10, further comprising:

prior to predicting effects of the treatment strategies, accounting for covariate imbalances by applying either inverse treatment propensity weighting (IPTW) or doubly robust average treatment effects to the control arm average treatment effect and the treatment arm average treatment effects.

16. A non-transitory computer readable storage medium storing one or more programs configured for execution by an electronic device with a display, the one or more programs comprising instructions for:

obtaining health trajectories for members of a healthcare system, wherein each health trajectory corresponds to a respective member and represents a time-ordered series of events for the respective member, and each event represents an interaction between the respective member and the healthcare system;

identifying index events in the health trajectories for the members, wherein an index event is any clinical or health data point;

segmenting the health trajectories with index events into a plurality of sub-trajectories such that each sub-trajectory ends at a different index event;

generating a digital fingerprint for each sub-trajectory by applying representation learning to generate an embedding vector, including training a code embedding machine learning model using at least a portion of the plurality of sub-trajectories to generate embedding vectors;

identifying one or more sub-trajectories that are similar to a patient sub-trajectory by performing a nearest-neighbor search on the embedding vectors of the members, wherein the patient sub-trajectory corresponds to a patient member of the healthcare system, wherein identifying the one or more sub-trajectories comprises:

selecting, from the plurality of sub-trajectories, one or more treatment sub-trajectories of the members that have taken a same prior treatment option as the patient member;

grouping the one or more treatment sub-trajectories into a control arm set of trajectories that includes sub-trajectories that continued taking the same treatment option as the same prior treatment option after an indexed event, and one or more treatment arm sets of trajectories that each include sub-trajectories that were prescribed a respective different treatment option after the indexed event;

computing a control arm average treatment effect for the control arm set of trajectories based on analyzing the sub-trajectories, in the control arm set of trajectories, after the indexed event;

computing a respective treatment arm average treatment effect, for each of the one or more treatment arm sets of trajectories, based on analyzing the respective sub-trajectories, in the respective treatment arm sets of trajectories, after the indexed event; and predicting effects of the treatment strategies by averaging the control arm average treatment effect and the treatment arm average treatment effects; and identifying treatment strategies that are most likely to be efficacious for the patient member based on outcomes associated with each of the treatment strategies, according to the one or more sub-trajectories, wherein applying representation learning comprises:

obtaining code embeddings corresponding to claim codes representing events in a sub-trajectory;

inputting the code embeddings to a recurrent neural network (RNN) to obtain hidden states for different layers for a terminal index event, wherein the RNN back-propagates error while learning embeddings during training; and combining the hidden states for different layers of the RNN to obtain the embedding vectors for the sub-trajectory.

* * * * *